US 6,728,573 B1

(12) United States Patent
Beck et al.

(10) Patent No.: US 6,728,573 B1
(45) Date of Patent: Apr. 27, 2004

(54) OCULAR IONTOPHORETIC APPARATUS HANDLE

(75) Inventors: Jon E. Beck, Salt Lake City, UT (US); Alexander K. Koss, Salt Lake City, UT (US)

(73) Assignee: Iomed, Inc., Salt Lake City, UT (US)

( * ) Notice: Subject to any disclaimer, the term of this patent is extended or adjusted under 35 U.S.C. 154(b) by 0 days.

(21) Appl. No.: 09/599,245

(22) Filed: Jun. 22, 2000

Related U.S. Application Data
(60) Provisional application No. 60/184,498, filed on Feb. 23, 2000.

(51) Int. Cl.[7] .................................................. A61N 1/30
(52) U.S. Cl. ........................... 604/20; 604/21; 604/294; 604/295; 604/298; 604/300
(58) Field of Search ................... 604/20, 21, 294, 604/295, 298, 300

(56) References Cited

U.S. PATENT DOCUMENTS

| | | | |
|---|---|---|---|
| 2,525,381 A | 10/1950 | Tower | |
| 3,122,137 A | 2/1964 | Erlanger | |
| 3,392,725 A | * 7/1968 | Behney | ................. 604/301 |
| 4,955,378 A | 9/1990 | Grasso | |
| 5,053,000 A | 10/1991 | Booth et al. | |
| 5,169,384 A | 12/1992 | Bosniak et al. | |
| 5,174,304 A | 12/1992 | Latina et al. | |
| 5,318,514 A | 6/1994 | Hofmann | |
| 5,618,274 A | * 4/1997 | Rosenthal | ................. 604/290 |
| 5,676,648 A | 10/1997 | Henley | |
| 5,908,401 A | 6/1999 | Henley | |
| 6,154,671 A | 11/2000 | Parel et al. | |
| 6,319,240 B1 | * 11/2001 | Beck | ................. 604/20 |

FOREIGN PATENT DOCUMENTS

| | | |
|---|---|---|
| EP | 0 529 510 A1 | 8/1992 |
| GB | 2 177 928 A | 2/1987 |
| WO | WO 96/36393 | 11/1996 |
| WO | WO 99/40967 | 8/1999 |

\* cited by examiner

*Primary Examiner*—Thomas Denion
*Assistant Examiner*—Theresa Trieu
(74) *Attorney, Agent, or Firm*—Factor & Lake

(57) ABSTRACT

An iontophoretic apparatus comprising a housing member, a current distribution member, a medicament containment member and a handle member. The current distribution member is associated with the housing member. The medicament containment member is associated with the current distribution member. The handle member is associated with the housing member. The handle member facilitates the positioning and placement of the iontophoretic apparatus.

6 Claims, 9 Drawing Sheets

OCULAR IONTOPHORETIC APPARATUS HANDLE

This application claims the priority of U.S. Provisional Application Serial No. 60/184,498 filed Feb. 23, 2000.

BACKGROUND OF THE INVENTION

1. Field of the Invention

The present invention is directed to ocular iontophoretic apparatuses, and more particularly, to a handle for an ocular iontophoretic apparatus to facilitate the grasping, positioning and placement thereof.

2. Background Art

The use of ocular iontophoretic devices has been known in the art. Such devices have been used in an attempt to administer a drug through an electromotive force which drives ionic chemicals through the eye tissue so that they can be absorbed by adjacent tissues and blood vessels.

Among other problems, difficulties can be incurred with the placement of these devices onto the surface of the eye of a patient. Specifically, in as much as certain of these devices are intended for use on only a portion of the eye, they are rather small in size. Accordingly, it is difficult for a doctor to carefully position the device in the proper orientation. Moreover, once placed on the patient's eye, it is often difficult to reposition or to adjust the positioning of the device.

Accordingly, it is an object of the invention to provide for a handle member which facilitates the grasping, positioning and placement of ocular iontophoretic apparatuses.

It is likewise an object of the invention to facilitate the repositioning of an ocular iontophoretic apparatus after placement onto the surface of the eye.

It is a further object of the invention to provide for a handle member which can be pinched so as to flex the iontophoretic apparatus during placement onto an eye and during removal from the eye of the patient.

These and other objects of the invention will become apparent in light of the specification and claims appended hereto.

SUMMARY OF THE INVENTION

The application comprises an iontophoretic apparatus which includes a housing member, a current distribution member, a medicament containment member and a handle member. The current distribution member is associated with the housing member. The medicament containment member is associated with the current distribution member. The handle member is associated with the housing member, and the handle member serves to facilitate the positioning and/or placement of the iontophoretic apparatus.

In a preferred embodiment, the handle member comprises a first handle region and a second handle region extending outwardly from the handle member. Each of the first and second handle regions are preferably co-molded with the housing member and distally spaced apart a predetermined distance. In one such embodiment, the first and second handle regions extend away from each other. In another embodiment, the handle member may be releasably associated with the housing member.

In another preferred embodiment, at least one of the first and second handle regions includes a gripping region. The gripping region facilitates the overall gripping of the handle region by a user during the positioning and/or placement of the apparatus. In another such embodiment, the first and second handle regions include a grasping region which joins the handle regions together to, in turn, render a single unitary handle region.

In another preferred embodiment, the first and second handle regions include means for flexing the housing member. In one such embodiment, the first and second handle regions further include means for limiting the flexing of the housing member. In one embodiment, the flexing limiting means may comprise the positioning of a portion of the first and second handle regions in a spaced apart orientation. The spaced apart orientation substantially corresponds to the desired maximum flex of the housing member.

In another such embodiment, the flexing limiting means further includes means for aligning the first and second handle regions. The aligning means precludes inadvertent misalignment of the first and second handle regions during flexing.

In another preferred embodiment, the apparatus further includes means for maintaining the registered placement of the apparatus in the desired orientation. In one such embodiment, the registered placement maintaining means may comprise a receiving region associated with one or both of the handle member and the housing member. In one such embodiment, the receiving region comprises at least one notch. Preferably, the apparatus may further include means for biasing at least a portion of the receiving region against the soft tissue of a user.

BEST MODE FOR PRACTICING THE INVENTION

Figure 1:
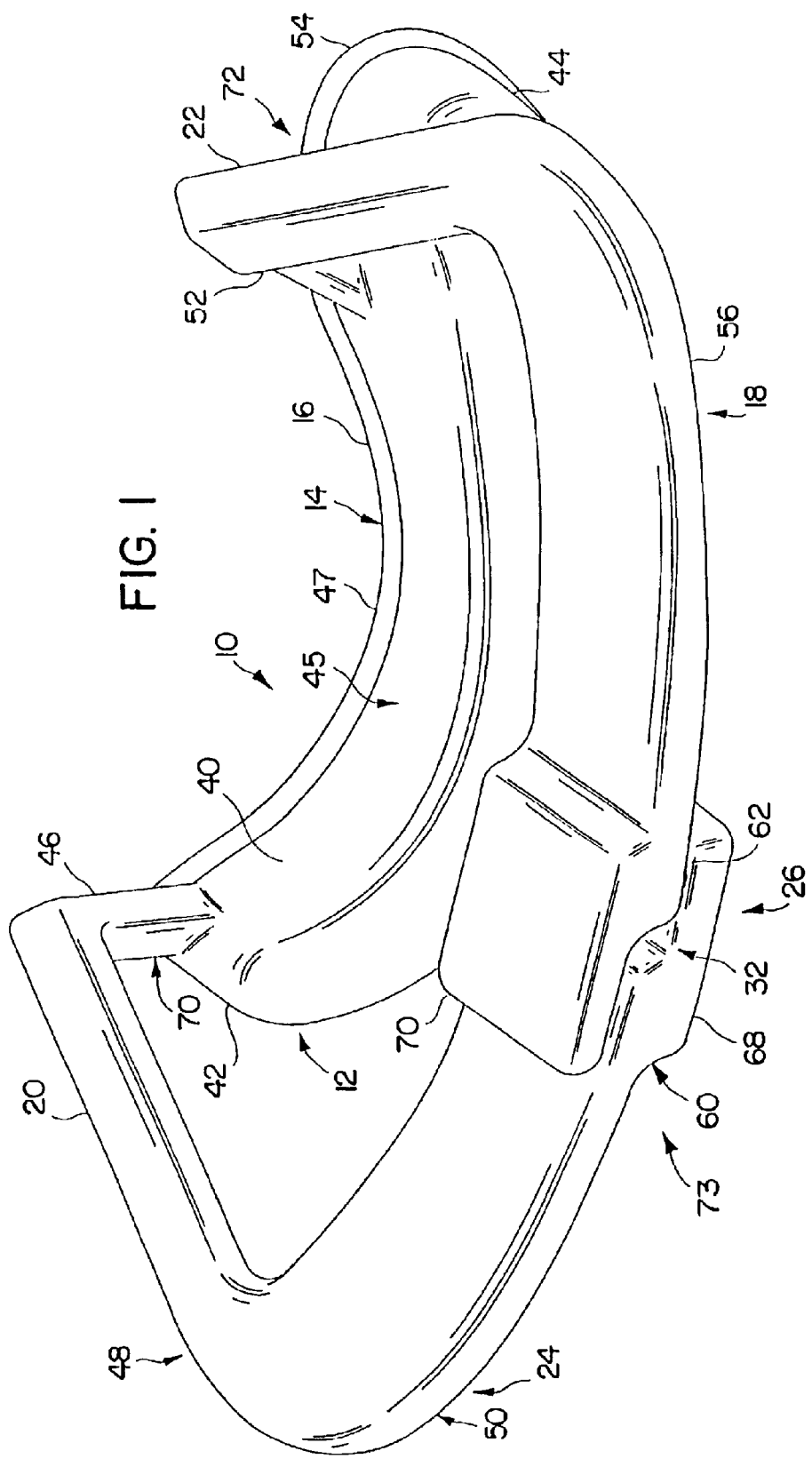
FIG. 1 of the drawings is a perspective view of the first embodiment of the apparatus of the present invention.

While this invention is susceptible of embodiment in many different forms, there is shown in the drawings and will be described in detail, several specific embodiments with the understanding that the present disclosure is to be considered as an exemplification of the principles of the invention and is not intended to limit the invention to the embodiments illustrated.

Figure 2:
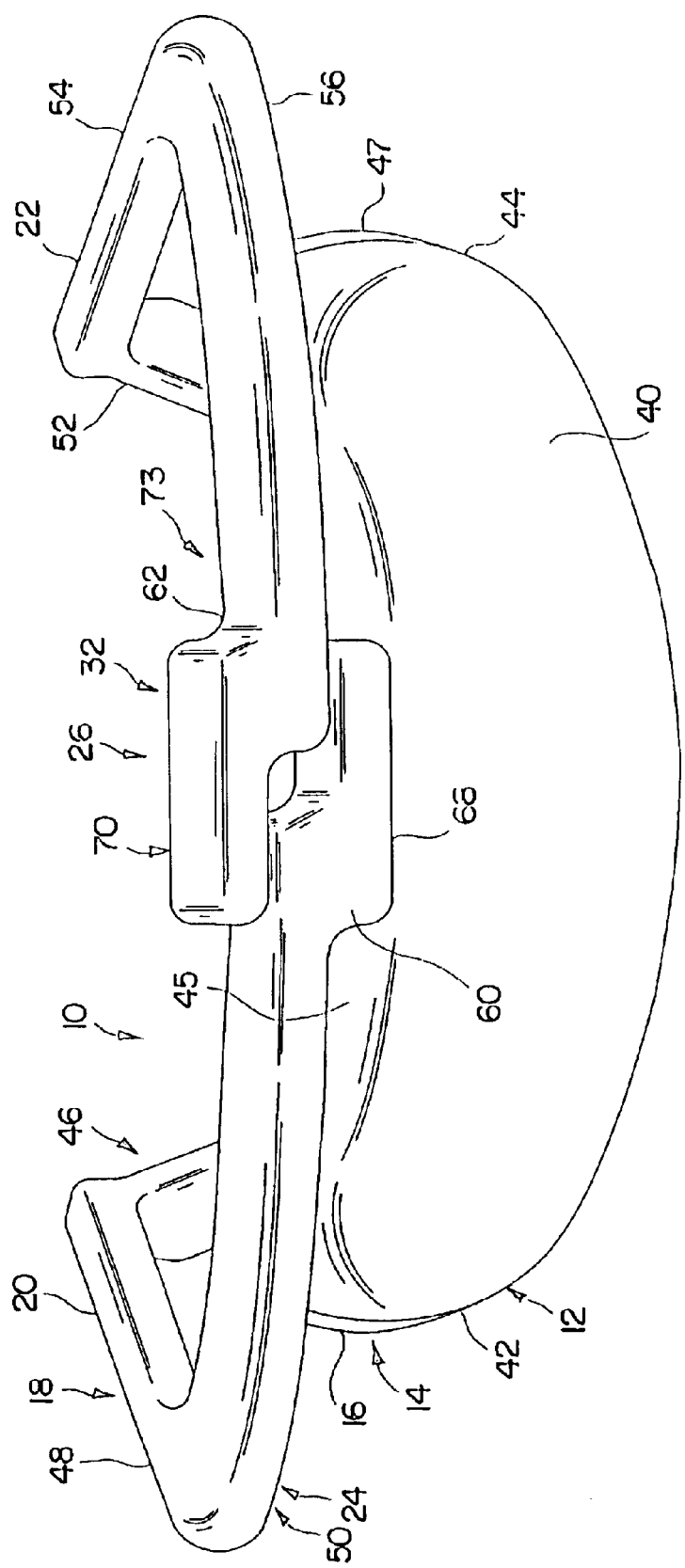
FIG. 2 of the drawings is a perspective view of the first embodiment of the apparatus of the present invention.

Iontophoretic apparatus 10 is shown in FIGS. 1 and 2 as comprising housing member 12, current distribution member 14, medicament containment member 16 and handle member 18. The housing member, the current distribution member and the medicament containment member are each described in detail in co-pending application Ser. No. 09/318,181 entitled "Methods and Apparatus for Ocular Iontophoresis," the complete specification of which is incorporated herein by reference. As described therein in greater detail, the housing member includes outer surface 40, first end 42, second end 44, upper region 45 and rim 47. Generally, the housing comprises a plastic material which is molded into a desired configuration for the positioning thereof on the eye of a patient.

As will be understood, housing member 12 may be of any number of sizes and shapes. Various embodiments of the housing member may include various configurations depending on the medicament to be dispensed, as well as the specific shape of the soft tissue surrounding the eye of the patient, and the particular region of the eye to which it is to be applied. Of course, the handle member is not limited to any particular housing member configurations and may be used with a wide variety of such devices. Additionally, the medicament that is retained in medicament containment member 16 for dispensing is not limited to any particular medicament, and virtually any medicament that can be applied iontophoretically through the eye can be used in association with the iontophoretic apparatus.

Figure 5:
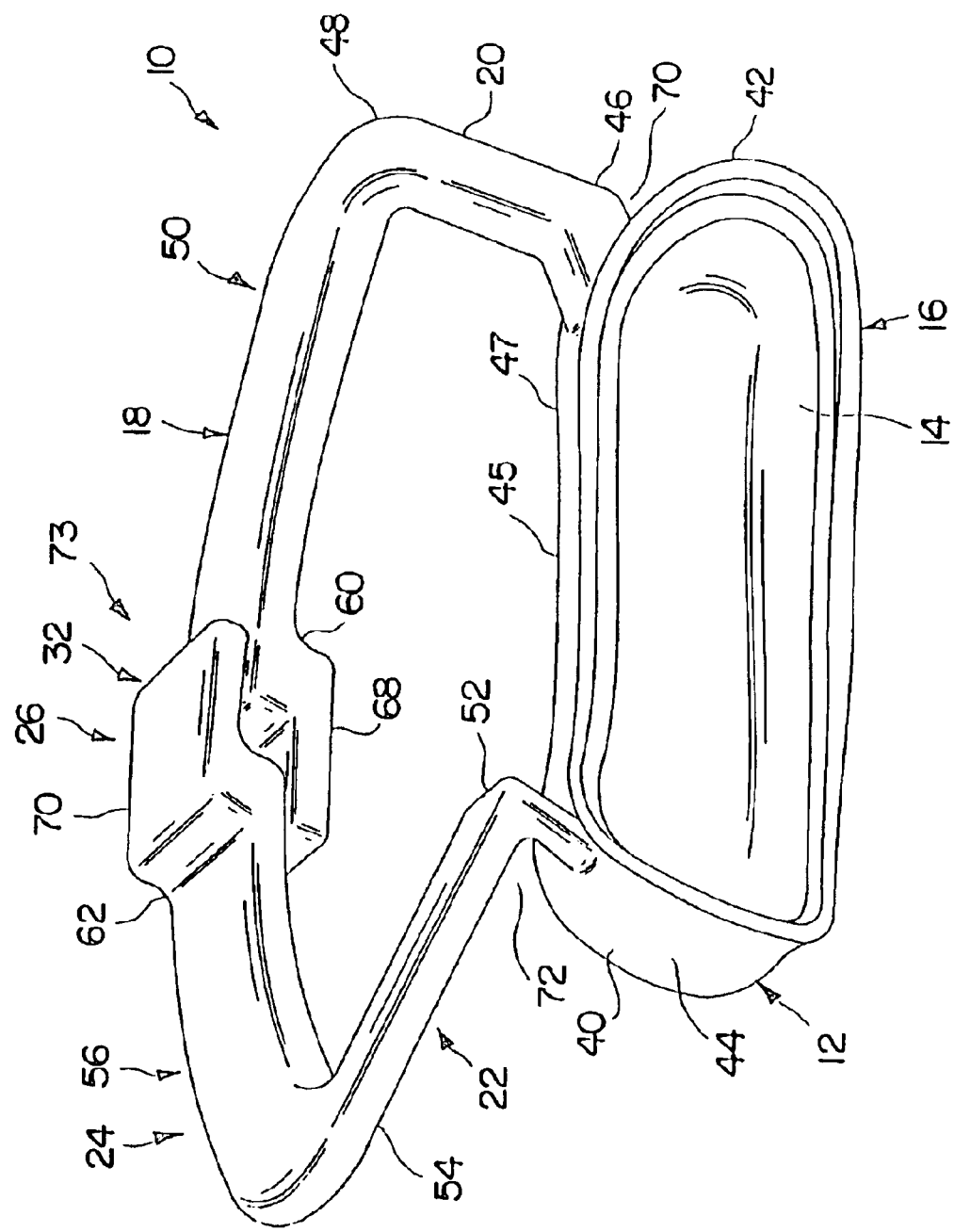
FIG. 5 of the drawings is a perspective view of the first embodiment of the apparatus of the present invention.

Handle member 18 is shown primarily in FIGS. 1 and 5 as comprising first handle region 20, second handle region 22, means 24 for flexing the handle member, means 26 for limiting the flexing of the handle member and means 25 for maintaining registered placement of the apparatus. Generally, handle member 18 is co-molded with housing member 12, however, it is likewise contemplated that the handle member may comprise a separate component which may be welded, adhered or otherwise joined to housing member 12. In addition, the handle member is generally associated with the upper region 45, which, in turn, facilitates placement of the device along, for example, the lower edge of the patient's eye under the lower eyelid. In addition, such handle positioning minimizes the intrusiveness of the handle member and the discomfort to the patient receiving treatment, while maximizing the versatility thereof.

Figure 3:
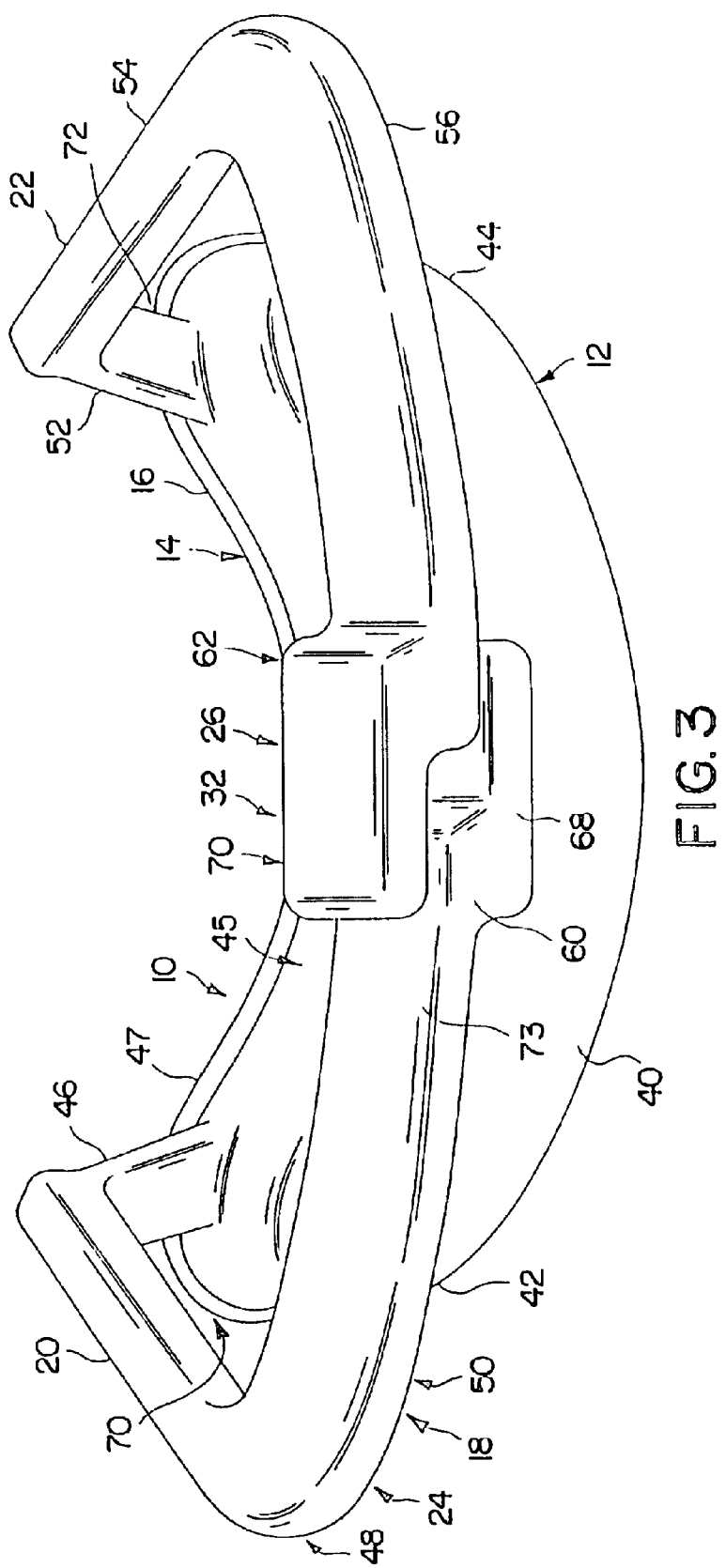
FIG. 3 of the drawings is a perspective view of the first embodiment of the apparatus of the present invention.
Figure 4:
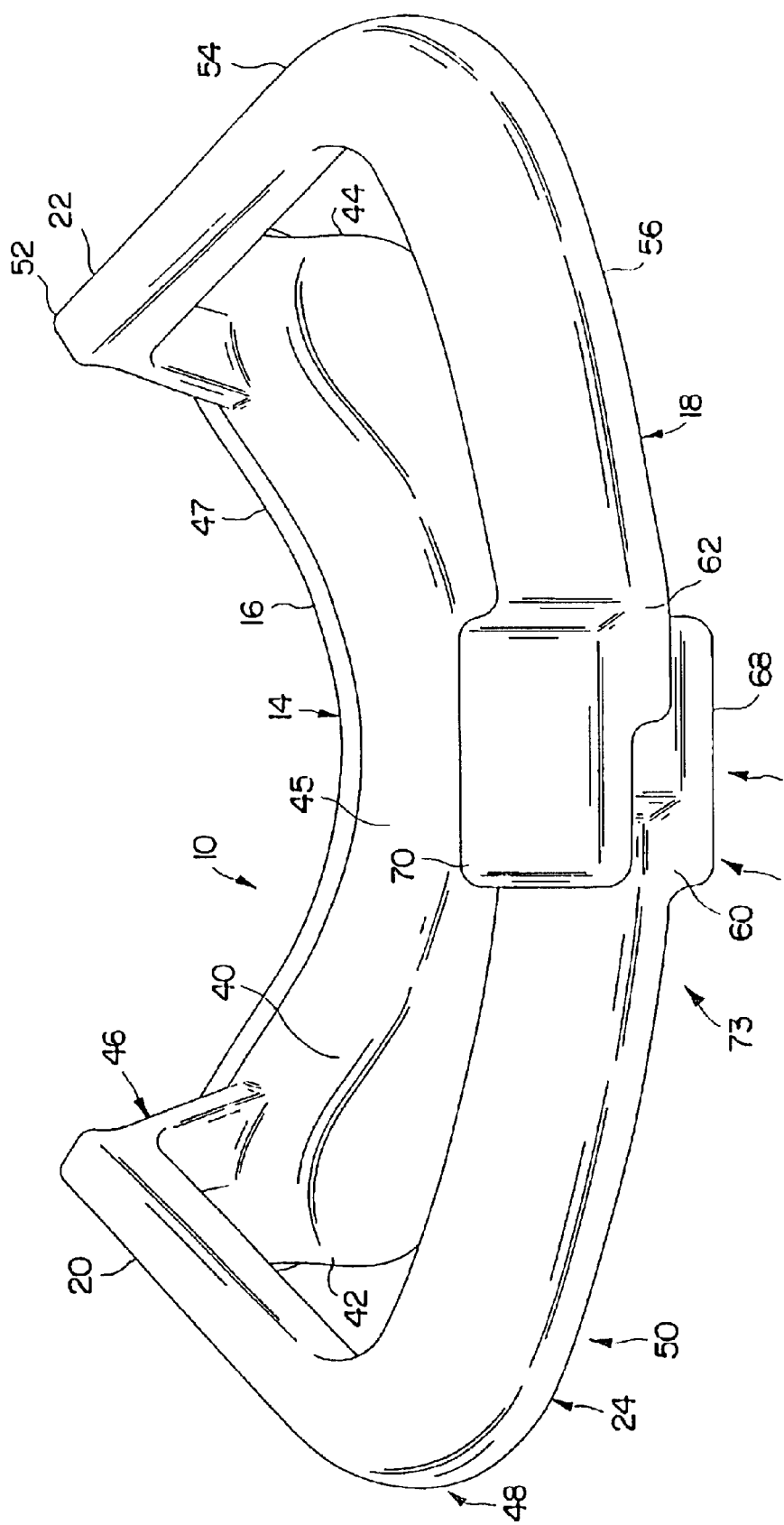
FIG. 4 of the drawings is a perspective view of the first embodiment of the apparatus of the present invention.
Figure 6:
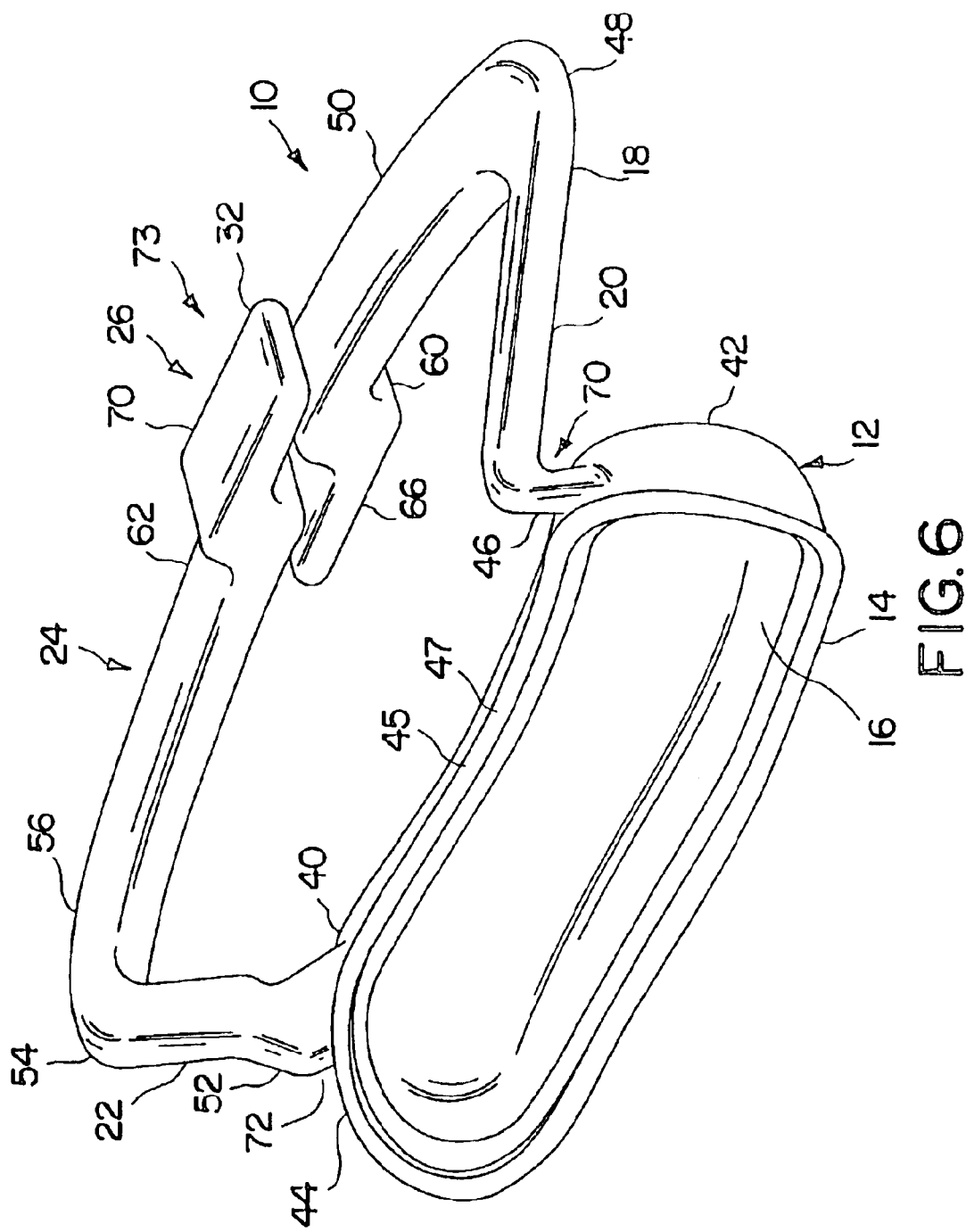
FIG. 6 of the drawings is a perspective view of the first embodiment of the apparatus of the present invention.
Figure 7:
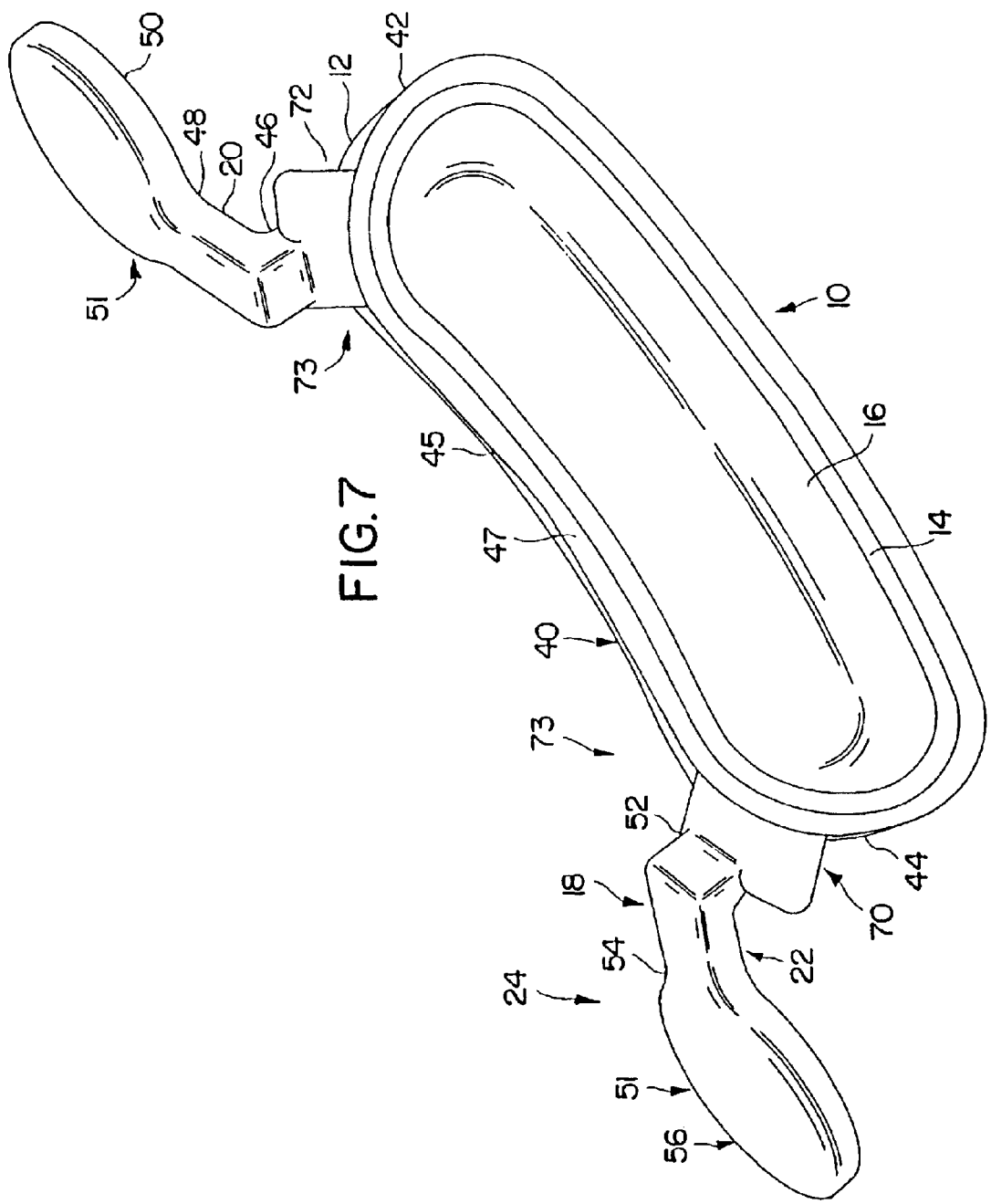
FIG. 7 of the drawings is a perspective view of a second embodiment of the apparatus of the present invention.

First handle region 20 of the handle member is shown in FIGS. 3 and 4 as including first end 46, second end 48 and first gripping portion 50. First end 46 is associated with outer surface 40 proximate first end 42 of the housing member. Second end 48 extends outwardly therefrom and in a direction which is generally away from second handle region 22 of the handle member. First gripping portion 50 is positioned proximate second end 48 of first handle region 20. Generally, first gripping portion 50 comprises a region which is sized and shaped so as to promote the gripping thereof by a doctor or other professional during placement of the iontophoretic apparatus in the eye of a patient. As can be seen in FIGS. 5 and 6, first gripping portion 50 is substantially planar and spaced apart from the housing member a distance sufficient to insure that the doctor can easily grip the gripping portion without inadvertently striking or touching the patient. In certain embodiments the gripping region comprises a substantially flat pod region 51 (FIG. 7).

It will be understood that second handle region 22 is substantially similar to first handle region 20, and comprises first end 52, second end 54 and second gripping portion 56. While various configurations are contemplated, generally, the first and second handle regions are substantial mirror images of each other (and are substantially symmetrical) about central axis 101 (FIG. 2) of the housing member.

Figure 8:
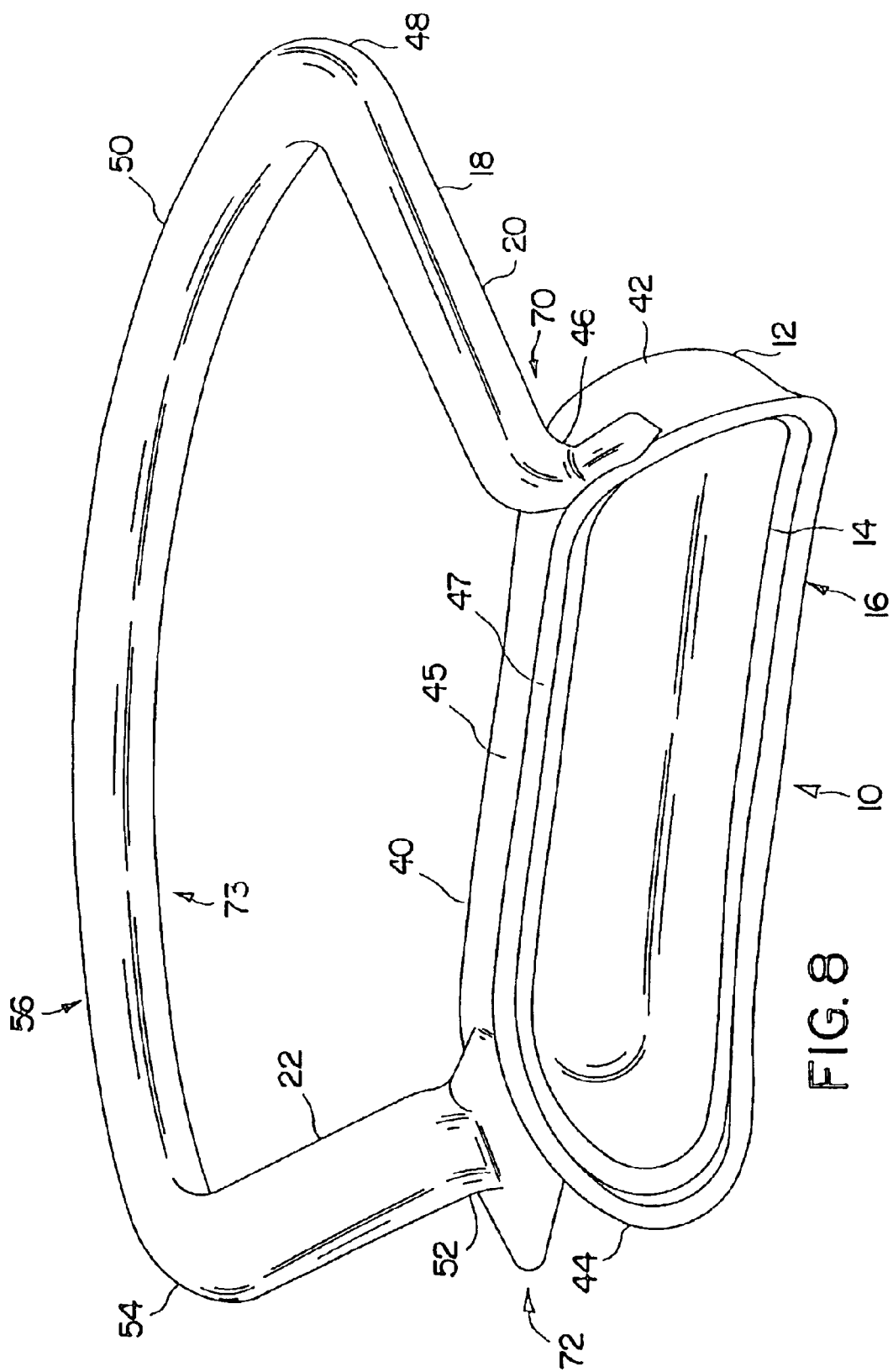
FIG. 8 of the drawings is a perspective view of a third embodiment of the apparatus of the present invention.

In the embodiment shown in FIG. 8, gripping portion 50 of first handle region 20 and gripping portion 56 of second handle region 22 are integrally associated with each other, to, in turn, define a single loop like configuration for the gripping portion. In such an embodiment, the integrated gripping portion extends from second end 48 of first handle region 20 to second end 54 of second handle region 22. The integrated gripping portion is substantially parallel to the housing member and generally follows the surface configuration of the outer surface 40 of housing member 12.

Figure 9:
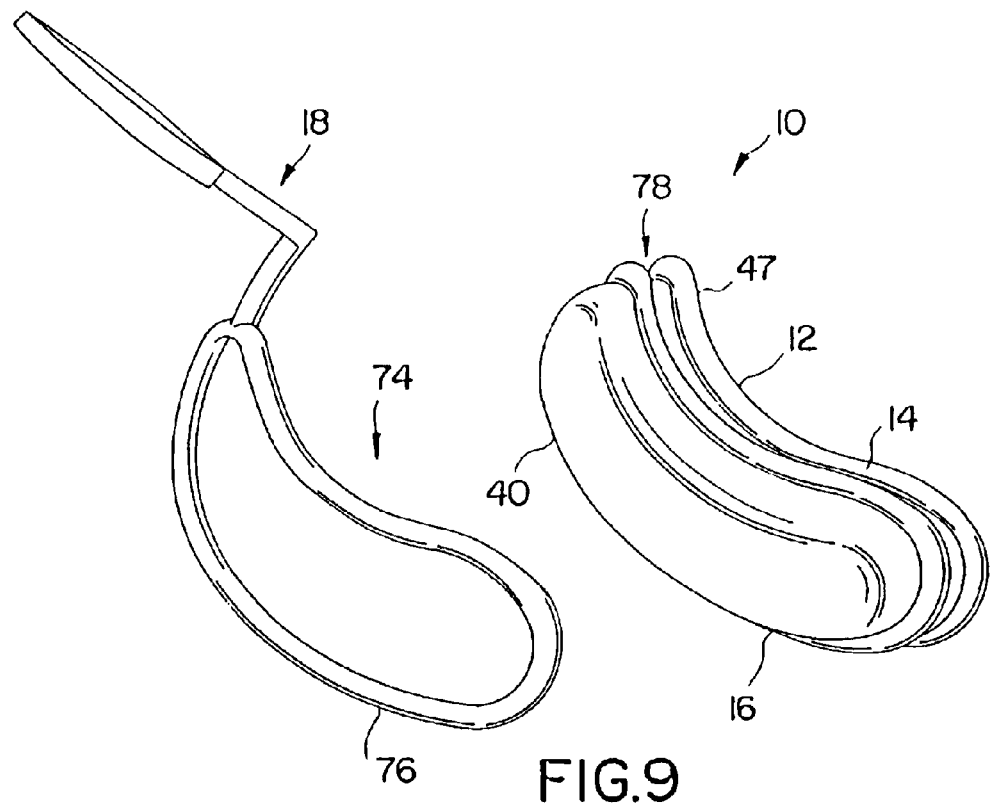
FIG. 9 of the drawings is a perspective view of a fourth embodiment of the apparatus of the present invention.
Figure 10:
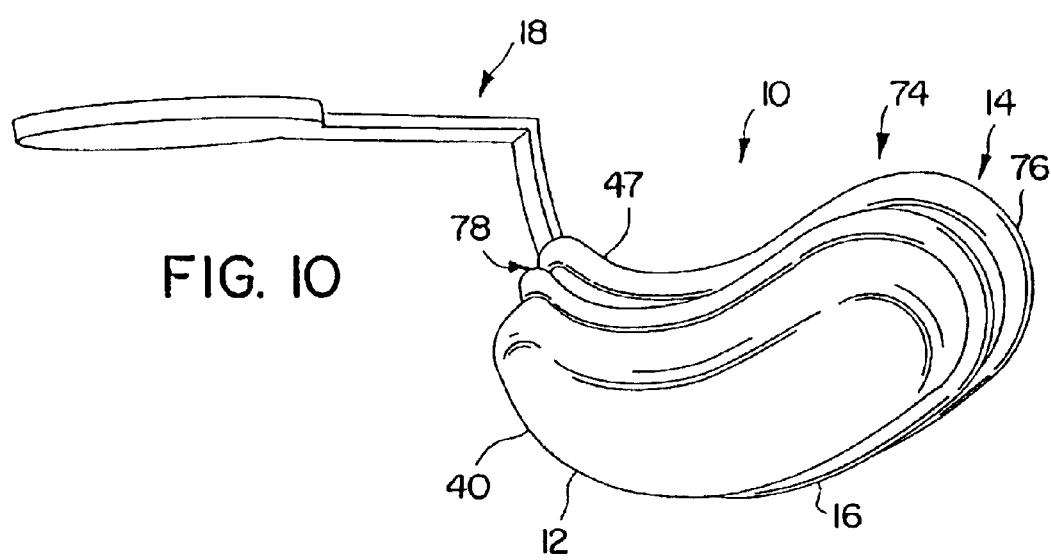
FIG. 10 of the drawings is a perspective view of the fourth embodiment of the apparatus of the present invention.

In the embodiment shown in FIGS. 9 and 10, handle member 18 may be removably associated with housing member 12. Specifically, in such an embodiment, handle member 18 includes means 74 for releasably retaining the handle member to the housing member. Releasable retaining means 74 includes hoop 76 which is releasably positionable within grooved recess 78 of the housing member. As will be understood, once the apparatus is positioned as desired in the eye, the handle member can be removed by pulling thereon, to, in turn, release hoop 76 from within recess 78 of the housing member. Additionally, it will be understood that while the removable handle member is shown as including a single gripping region, other handle members, including, but not limited to, those shown in FIGS. 1, 7 and 8 are likewise contemplated.

In the embodiment shown in FIGS. 5 and 6, gripping portion 50 of first handle region 20 and gripping portion 56 of second handle region 22 are spaced apart a predetermined distance from each other, to essentially provide a means for flexing the housing. Specifically, and as will be explained in more detail below with respect to the operation, as the doctor or professional pinches the first and second gripping portions 50, 56, about the respective second ends of handle regions 20, 22, toward each other, the force, in turn, flexes the housing member. By flexing the housing member during insertion and positioning on the surface of the eye, an improved fit, and an improved positioning can be achieved. Indeed, as long as the first and second gripping portions are not united to form a single integrated gripping portion, by positioning the first and second handle regions at opposite ends of the housing member, the pinching thereof will facilitate the flexing of the housing member.

Placement of a gap between the first and second gripping portions defines means 26 for limiting the flexing of the housing member. Specifically, gripping portion 50 and gripping portion 56 extend from the respective second ends of the respective handle regions so as to be substantially parallel to outer surface 40 of housing member 12. The two gripping portions essentially extend toward each other until end 60 of first gripping portion 50 is separated from end 62 of second gripping portion 56 by a gap. Thus, as the user pinches the gripping members, the distance separating the two gripping portions becomes smaller until end 60 of first gripping portion is in abutment with end 62 of second gripping portion 56. At such time, the respective gripping portions can be pinched no further and additional flexing of the housing member is not possible.

As shown in FIGS. 5 and 6, the flexing limiting means further includes means 32 for aligning the respective ends of the gripping portions. In particular, aligning means 32 includes first alignment member 68 which is associated with end 60 of gripping portion 50 and second alignment member 69 which is associated with end 62 of gripping portion 52. As will be understood, as the user flexes the ends, the alignment members insure that end 60 of gripping portion 50 is aligned with end 62 of gripping portion 52, so that the flexing can be limited by the interaction and abutment of the two ends. Indeed, without the alignment members, inadvertent misalignment of the ends would permit the flexing of the respective ends without limitation and beyond that which is desirable.

Placement registration means 25 is shown in FIG. 1 as including retaining regions 70, 72 and means 73 for biasing the retaining region against the soft tissue of a patient. Retaining region 70 is associated with one or both of first end 46 of first handle region 20 and first end 42 of housing member 12. Similarly, retaining region 72 is associated with one or both of first end 52 of second handle region 22 and second end 44 of housing member 12. The retaining regions comprise structures, such as notches that are configured to cooperate with the corner area of the soft tissue surrounding the eye of the user. Biasing means 73 comprises the natural resilience of the material surrounding retaining region 70 to return to its original configuration upon flexing thereby biasing the retaining regions against the soft tissue of a patient. As will be explained, the corner areas of the eye, the retaining regions and the biasing means cooperate to maintain the registered placement of the apparatus in the desired orientation, and substantially preclude movement of the apparatus once positioned. It is also contemplated that the placement registration means is not limited to cooperation with the corners of the eyes; rather, it can also cooperate with other surrounding tissues that remain substantially static during movement of the eye.

It is additionally contemplated that the electrical leads which attach the power supply to the electrodes which drive the medicament may be molded into the handle member.

In operation, the doctor, physician's assistant or other professional first selects the appropriate apparatus from among various apparatuses of different size, shape and medicament. As explained above, the apparatus is not limited to any particular shape and any particular medicament. Once selected and prepared for placement by the doctor or assistant on the patient's eye, the apparatus is grasped by the gripping members and positioned onto the surface of the eye.

In particular, in the embodiment shown in FIG. 1, the doctor first pinches the respective gripping portions 50, 56 toward each other so as to flex housing member 12. Once flexed as desired, the user positions the housing member on the surface of the patient's eye. As the initial contact with the surface of the eye is attained, the doctor slowly releases the pinching grip on the gripping regions, and housing member 12 returns to its original orientation at which time the entire outer rim 46 is in contact with the surface of the eye. By pinching the gripping regions prior to positioning, improved surface mating between the outer rim and eye and improved comfort to the patient is achieved. Moreover, better control can be maintained over the apparatus, which, in turn, facilitates improved accuracy relative to placement on the surface of the eye.

In addition, as the doctor releases the handle member, the corner regions of the eye are positioned into and accepted by retaining regions 70 and 72 of registered placement maintaining means 25 so as to achieve registered placement of the apparatus in the desired orientation.

Furthermore, biasing means 73 of registered placement maintaining means 25 cooperates with the retaining regions to bias and, in turn, maintain the corner of the eye and the retaining regions in cooperative engagement. The cooperation of the registered placement maintaining means and the biasing means can also compensate for size variation in the dimensions of the soft tissue surrounding the eye. In certain embodiments, biasing means 73 and the flexing means of the handle member may be integrated into a single structure.

Once fully positioned, the doctor initiates current delivery from the current distribution member. The current forces medicament retained in the medicament containment member through the tissue of the patient's eye. The treatment continues for a predetermined period of time which is determined by the type and quantity of medicament that is to be transmitted to the patient.

Once the treatment is complete, current ceases to be delivered by the current distribution member. At such time, passage of medicament through the patient's tissue ceases. When the treatment is complete, the apparatus can be removed from the patient. Specifically, the doctor again grasps the gripping regions of handle member 12 and pulls the housing from the surface of the eye.

In the embodiment shown in FIG. 1, the user pinches gripping portions 50 and 56 until housing member 12 flexes. The flexing of the housing member likewise facilitates the release of the housing member from the surface of the eye in a controlled manner.

In the embodiment shown in FIG. 7, the user may individually grasp each of the separate gripping members to release the housing member from the surface of the eye. Similarly, in the embodiment of FIG. 8, the doctor can grab the unitized gripping member to release the housing member from the surface of the eye.

The foregoing description merely explains and illustrates the invention and the invention is not limited thereto except insofar as the appended claims are so limited, as those skilled in the art who have the disclosure before them will be able to make modifications without departing from the scope of the invention.

What is claimed is:

1. A method for improving the placement, positioning, registration and securement of an iontophoretic device, the device including a housing member, a current distribution member associated with the housing member, and a handle member releasably associated with the housing member, the method comprising the steps of:

grasping the handle member;

flexing the housing member;

using the handle member, positioning and applying the housing member, when flexed, on a predetermined surface area of an eye;

releasing the flex of the housing member to, in turn, secure and register the placement and positioning of the housing member on the eye surface; and removing the handle member from the housing member.

2. The method according to claim 1, wherein the handle member comprises a first handle region and a second handle region extending outwardly from the handle member, and the step of grasping comprises the step of grasping the first and second handle members separately, and the step of flexing comprises the step of manipulating the first and second handle members towards each other.

3. The method according to claim 2, wherein the step of flexing the housing member comprises the step of limiting the flex of the housing member.

4. The method according to claim 3, wherein the step of limiting the flex comprises the step of placing the first and second handle regions a predetermined distance apart.

5. The method according to claim 1, wherein at least one of the housing member and the handle member comprise a receiving region which cooperates with a predetermined portion of the soft tissue of the eye, the step of positioning and applying the housing member comprising the step of aligning the receiving region with the predetermined portion of the eye.

6. The method according to claim 5, wherein the method further comprises the step of biasing at least a portion of the receiving region against at least a portion of the soft tissue of the eye.

* * * * *